United States Patent
Braam et al.

(10) Patent No.: US 11,773,375 B2
(45) Date of Patent: Oct. 3, 2023

(54) IN VIVO METHOD FOR DIFFERENTIATING HUMAN PLURIPOTENT STEM CELLS INTO ATRIAL CARDIOMYOCYTES

(71) Applicant: Ncardia B.V., Leiden (NL)

(72) Inventors: Stefan Robbert Braam, Leiden (NL); Ana Catarina Martins Grandela, Leiden (NL); Karin Langenberg, Leiden (NL)

(73) Assignee: Ncardia B.V., Leiden (NL)

( * ) Notice: Subject to any disclaimer, the term of this patent is extended or adjusted under 35 U.S.C. 154(b) by 2 days.

(21) Appl. No.: 16/088,227

(22) PCT Filed: Mar. 27, 2017

(86) PCT No.: PCT/NL2017/050190
§ 371 (c)(1),
(2) Date: Sep. 25, 2018

(87) PCT Pub. No.: WO2017/164746
PCT Pub. Date: Sep. 28, 2017

(65) Prior Publication Data
US 2020/0216812 A1 Jul. 9, 2020

(30) Foreign Application Priority Data

Mar. 25, 2016 (NL) .................................. NL2016496

(51) Int. Cl.
*C12N 5/077* (2010.01)

(52) U.S. Cl.
CPC ........ *C12N 5/0657* (2013.01); *C12N 2500/38* (2013.01); *C12N 2501/155* (2013.01); *C12N 2501/999* (2013.01); *C12N 2506/45* (2013.01)

(58) Field of Classification Search
None
See application file for complete search history.

(56) References Cited

U.S. PATENT DOCUMENTS

2009/0155831 A1 * 6/2009 Nistor .................. C12N 5/0657
435/29

FOREIGN PATENT DOCUMENTS

| WO | WO-2008112323 A1 * | 9/2008 | ........... C12N 5/0657 |
|---|---|---|---|
| WO | WO 2011/157029 | 12/2011 | |
| WO | WO 2014/078414 | 5/2014 | |
| WO | WO-2014075414 A1 * | 5/2014 | ................ H02P 4/00 |

OTHER PUBLICATIONS

Kattman et al Cell Stem Cell 8, 228-240 (Year: 2011).*
Karakikes et al Stem Cells Transl Med. Jan;3(1):18-31 (Year: 2014).*
Yang et al Nature. May 22; 453(7194):524-8 (Year: 2008).*
Mikels et al.,Oncogene, 25: 7461-7468 (Year: 2006).*
Dravid et al., Stem Cells, 23: 1489-1501 (Year: 2005).*
Meijer et al., Trends in Pharmacological Sciences, 25(9): 4 71-480 (Year: 2004).*
Zhang et al Cell Research 21:579-587 (Year: 2011).*
Devalla et al EMBO molecular medicine, vol. 7 (issue 4), pp. 394-410 (Year: 2015).*
Devella et al EMBO Molecular Medicine, 7, 394-410 (Year: 2015).*
Elliott et al Nature Methods, 8(12), 1037-1040 (Year: 2011).*
Denning et al., Cardiomyocytes from human pluripotent stem cells: From laboratory curiosity to industrial biomedical platform. Biochim Biophys Acta. Jul. 2016;1863(7 Pt B):1728-48.
Devalla et al., Atrial-like cardiomyocytes from human pluripotent stem cells are a robust preclinical model for assessing atrial-selective pharmacology. EMBO Mol Med. Apr. 2015;7(4):394-410.
Zhang et al., Direct differentiation of atrial and ventricular myocytes from human embryonic stem cells by alternating retinoid signals. Cell Res. Apr. 2011;21(4):579-87.
International Search Report and Written Opinion for PCT/NL2017/050190, dated May 29, 2017, 10 pages.

* cited by examiner

*Primary Examiner* — Anoop K Singh
(74) *Attorney, Agent, or Firm* — CASIMIR JONES, S.C.; Tanya A. Arenson

(57) ABSTRACT

The present invention is in the field of pluripotent stem cells, more particularly cardiomyocytes derived from pluripotent stem cells. The present invention provides a novel method for differentiating human pluripotent stem cells into a population of cardiomyocytes having an atrial phenotype, and use of said atrial cardiomyocytes for screening of drugs, AF disease model, and others. The method of the invention is particularly useful to generate cardiomyocytes having a more developed or mature atrialphenotype and/or to generate higher yield of cardiomyocytes having an atrialphenotype.

13 Claims, No Drawings

IN VIVO METHOD FOR DIFFERENTIATING HUMAN PLURIPOTENT STEM CELLS INTO ATRIAL CARDIOMYOCYTES

FIELD OF THE INVENTION

The present invention is in the field of pluripotent stem cells, more particularly cardiomyocytes derived from pluripotent stem cells. The present invention provides a novel method for differentiating human pluripotent stem cells into a population of cardiomyocytes having an atrial phenotype, and use of said atrial cardiomyocytes for screening of drugs (e.g. AF drugs), AF disease models, and others. The method of the invention is particularly useful to generate cardiomyocytes having a more developed or mature atrial phenotype and/or to generate higher yield of cardiomyocytes having an atrial phenotype.

BACKGROUND OF THE INVENTION

The advent of pluripotent stem cells in medicine, such as induced pluripotent stem cells and embryonic pluripotent stem cells, has opened new avenues for research and therapeutic applications in general.

One main application of pluripotent stem cells (e.g. human induced pluripotent stem cells) is their use in in vitro culture system for generating cardiomyocytes, particularly human cardiomyocytes. Culture-derived (human) cardiomyocytes have various utilities ranging from drug screening, drug discovery, tissue engineering, tissue repair, disease model, fundamental research into the study of mechanisms underlying cardiac diseases, translational research, and many others.

Current in vitro culture systems, relying on the use of human pluripotent stem cells (for instance human induced pluripotent stem cells (hiPSC)), may yield population of cardiomyocytes that are heterogeneous in nature. More specifically, it was found that cardiomyocytes derived from differentiating pluripotent stem cells in traditional in vitro culture system may consist of a mixture of three different cardiomyocytes subtypes, namely embryonic atrial, ventricular and nodal cardiomyocytes. Each subtype is characterized by a unique phenotype in terms of morphology, gene expression patterns and cellular function (e.g. electrophysiology, contractile force, calcium metabolism, etc).

Heterogeneity of pluripotent stem cell-derived cardiomyocytes, as can be obtained from traditional in vitro culture system, is problematic as it may cause undesired effects such as ventricular arrhythmias when used in the context of cardiac repair or biased, insensitive or unwanted drug reaction or effects when used in the context of drug screening/discovery, and others. In addition, it hampers research on and use of specific subtypes, for example on atrial cardiomyocytes.

Therefore, there is a need for reducing the heterogeneity of pluripotent stem cell-derived cardiomyocyte populations in in vitro culture system so as to remedy the limitations discussed above.

More particularly, there is a need for in vitro culture systems devoid of the limitations above and which further allow to specifically generate populations of cardiomyocytes with an atrial phenotype, i.e. atrial cardiomyocytes.

Pluripotent stem cell-derived cardiomyocytes with an atrial phenotype would be particularly advantageous, for instance, in the context of drug screening for diseases such as atrial fibrillation (AF), a condition that affects over 33 million people globally, and for which no satisfactory or safe drug treatment (e.g. antiarrhythmic drugs) is currently available.

Pluripotent stem cell-derived cardiomyocytes with an atrial phenotype would also be particularly advantageous for generating new disease models for AF. Recent genome-wide association studies have identified genetic variants in a number of chromosomal regions that are associated with AF) (e.g. PITX2, CAV1, MYOZ1, C9orf3 and FANCC, and others). Pluripotent stem cells (e.g. iPSC) derived from AF patients carrying one or genetic variants may be used as a source to generate cardiomyocytes with an atrial phenotype for research purposes and/or drug screening, and others.

Recent advances have been made on these fronts. For instance, U.S. Pat. No. 9,273,286 discloses a method for generating atrial cardiomyocytes from stem cells in culture, which method comprises: 1) contacting the stem cells with bFGF and BMP 4; 2) contacting the stem cells treated by bFGF and BMP 4 with activin A; 3) contacting the stem cells that have been treated by activin A with Noggin; 4) stimulating or not inhibiting retinoic acid signaling pathway in the stem cells treated by Noggin; and 5) contacting the stem cells treated by Noggin with DKK1. However, the method described in U.S. Pat. No. 9,273,286 is not optimal as it is associated with low differentiation efficiency and low yield of atrial cardiomyocytes.

A further method for generating atrial cardiomyocytes from pluripotent stem cells in culture is disclosed in Devalla et al (2015) EMBO molecular medicine, Vol. 7 (issue 4), pages 394-410. Briefly, the method consists of treating hESCs with ACT-A, BMP4, CHIR-99021, SCF and VEGF for 4 days, so as to induce differentiation (i.e. until the stage of mesoderm formation), followed by treatment with a retinoic acid compound for 3 days. However, the method described in Devalla et al suffers from the same limitations identified above, i.e. low differentiation efficiency and low yield of atrial cardiomyocytes.

Therefore, there is a need for alternative in vitro culture systems, which are devoid of the limitations above, i.e. 1) allow reducing the heterogeneity of pluripotent stem cell-derived cardiomyocyte populations in in vitro culture system, 2) allow to specifically generate (more homogenous) populations of cardiomyocytes with an atrial phenotype, 3) allow to specifically generate populations of cardiomyocytes having a more developed or mature (e.g. adult-like) atrial phenotype, and/or 4) allow generating higher differentiation efficiency and/or higher yield of atrial cardiomyocytes from pluripotent embryonic stem cells. Preferably such methods may be performed within the same time periods as those typically observed in the art, preferably within a shorter time period.

DESCRIPTION OF THE INVENTION

Definitions

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

"A," "an," and "the": these singular form terms include plural referents unless the content clearly dictates otherwise. Thus, for example, reference to "a cell" includes a combination of two or more cells, and the like.

"About" and "approximately": these terms, when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Comprising": this term is construed as being inclusive and open ended, and not exclusive. Specifically, the term and variations thereof mean the specified features, steps or components are included. These terms are not to be interpreted to exclude the presence of other features, steps or components.

"Cardiomyocytes" or "cardiac myocytes": This refers to any cardiomyocyte lineage cells, and can be taken to apply to cells at any stage of cardiomyocyte ontogeny, unless otherwise specified. For example, cardiomyocytes may include both cardiomyocyte precursor or progenitor cells (i.e. cells that are capable, without dedifferentiation or reprogramming, of giving rise to progeny that include cardiomyocytes, e.g. immature cardiomyocytes or foetal cardiomyocytes) and mature cardiomyocytes (adult-like cardiomyocytes). Cardiomyocytes include atrial type cardiomyocytes, ventricular type cardiomyocytes, and nodal type cardiomyocytes and/or conducting system cardiomyocytes (see e.g. Maltsev et al, Mech Dev. 1993 November; 44(1):41-50 or Cardiac Regeneration using Stem Cells (10 Apr. 2013); Keiichi Fukuda, Shinsuke Yuasa CRC Press. ISBN 9781466578401). The cardiomyocyte progenitors, like the mature cardiomyocytes, may express markers typical of the cardiomyocyte lineage, including, without limitation, alpha actinin, cardiac troponin I (cTnI), cardiac troponin T (cTnT), sarcomeric myosin heavy chain (MHC), GATA-4, Nkx2.5, N-cadherin, β1-adrenoceptor (β1-AR), ANF, the MEF-2 family of transcription factors, creatine kinase MB (CK-MB), myoglobin, or atrial natriuretic factor (ANF).

"Cardiomyocyte subtypes" or "pluripotent stem cell-derived cardiomyocytes subtypes": This term refers to the three major subtypes of human pluripotent stem cell-derived cardiomyocytes that have an atrial, ventricular, or nodal phenotype, for example as determined by profile of gene or protein expression, cell surface expression of markers, electrophysiological profile, action potential (AP), responsiveness to cardioactive drugs (e.g. beating frequency, contractility etc) or based on other features or characteristics known in the art to be characteristic of a particular cardiomyocytes subtype. The skilled person is well-acquainted with methods for establishing whether and/or when a pluripotent stem cell-derived cardiomyocytes has acquired an atrial, ventricular, or nodal phenotype. For instance, pluripotent stem cell-derived cardiomyocytes having a atrial phenotype can be identified in the method as taught herein by detecting alteration in the expression level of certain gene markers such as, but not limited to, COUP-TFI and II or by detecting the presence (e.g. using conventional methods such as gene expression analysis, in situ hybridization, mRNA probes, immunohistochemistry, etc) of COUP-TFI and/or II on or in a cell. Additionally, also other markers such as for example SLN, NPPA, KCNA5 and PITX2, HAND1, HEY2, IRX4 and/or MYL2 and others, such as described in Van Der Berg (2015) Development, Vol. 142, pages 3231-3238, may be measured (e.g. by gene expression analysis, flow cytometry, in situ hybridization, mRNA probes, immunohistochemistry, etc). In other instances, detection or measurement of an up-regulation of atrial transcripts such as, but not limited to, COUP-TFI and II may be performed to identify cardiomyocytes having an atrial phenotype, i.e. atrial cardiomyocytes within the context of the current invention. Additionally, the up-regulation of other markers such as for example SLN, KCNA5, NPPA and PITX2 along with a down-regulation of ventricular transcripts such as HAND1, HEY2, IRX4 and MYL2, can also be used as an indication that a pluripotent stem cell-derived cardiomyocyte has acquired an atrial phenotype.

"Atrial phenotype" or "pluripotent stem cell-derived cardiomyocytes having an atrial phenotype or "atrial-like phenotype": The term refers to pluripotent stem cells which have differentiated into atrial cardiomyocytes, or at least into cell displaying atrial characteristics, for example as obtained by the methods of the invention. The cells display or express atrial markers such as, but not limited to, COUP-TFI and/or II, as taught above. The pluripotent stem cell-derived cardiomyocytes having an atrial phenotype obtained by the methods of the invention typically display or express atrial markers such as, but not limited to, COUP-TFI and/or II, at about 7, 8, 9, 10, 11, 12, 13, more preferably 14 days or later after initiating step a) of the methods as taught herein. In other words, the pluripotent stem cell-derived cardiomyocytes having an atrial phenotype obtained by the methods of the invention are induced to undergo atrial differentiation or are induced to take a developmental pathway leading to atrial differentiation as a result of steps a) and b) of the method of the invention but may display an atrial phenotype (e.g. as exemplified by, for example, the expression of atrial markers like COUP-TFI and/or COUP-TFII) after steps a) and b), i.e. at about 7, 8, 9, 10, 11, 12, 13, more preferably 14 days or later after initiating step a). Preferably, the atrial phenotype is confirmed by detecting or measuring the co-expression or co-presence of COUP-TFI and/or COUP-TFII with another cardiomyocyte markers, such as those taught herein, e.g. COUP-TFI and/or COUP-TFII with alpha actinin, in the pluripotent stem cell-derived cardiomyocytes obtained by the methods of the invention, at about 7, 8, 9, 10, 11, 12, 13, more preferably 14 days or later after initiating step a). Typically, the cells may show contractions (i.e. are "beating"). The term "atrial phenotype" also means that the pluripotent stem cell-derived atrial cardiomyocytes obtained by the methods of the present invention are similar or resemble mature or adult atrial cardiomyocytes in terms of typical atrial morphology, functions, e.g. electrophysiological activity, action potential (AP) shape, ion channel expression and function, contractibility, beat frequency etc, gene expression profile (e.g. COUP-TFI And/or II, KCNA5, cell surface markers, and/or others). In the present invention, pluripotent stem cell-derived cardiomyocytes having an atrial phenotype are considered to be "atrial cardiomyocytes".

"COUP-TFI and COUP-TFII": These terms refer to COUP transcription factor 1 and 2, respectively. COUP-TFI and II are known as NR2F1 (nuclear receptor subfamily 2, group F, member 1) and NR2F2 (nuclear receptor subfamily 2, group F, member 2), respectively. In humans, COUP-TFI and COUP-TFII are proteins encoded by the NR2F1 and NR2F2 genes, respectively. The COUP acronym stands for "chicken ovalbumin upstream promoter". Both COUP-TFI and COUP-TFII have been shown to be essential for conferring the identity of atrial cardiomyocytes, promotes atrial genes while suppressing ventricular gene expression, as well as controlling a broad range of functions in cardiomyocytes (Wu et al (2013) Dev Cell, Vol. 25(4), pages 417-26). Further, it was shown that COUP-TFI and COUP-TFII play a role in inducing or promoting an atrial phenotype in pluripotent stem cell-derived cardiomyocytes. Both COUP-TFI and COUP-TFII have been shown to be robust markers of pluripotent stem cell-derived cardiomyocytes having acquired an atrial phenotype (Devalla et al (2015) EMBO molecular medicine, Vol. 7 (issue 4), pages 394-410).

"Conventional techniques" or "methods known to the skilled person": These terms refer to a situation wherein the methods of carrying out the conventional techniques used in methods of the invention will be evident to the skilled worker. The practice of conventional techniques in molecular biology, biochemistry, cell culture, genomics, sequencing and related fields are well-known to those of skill in the art and are discussed, for example, in the following literature references: Human Embryonic Stem Cell: The Practical Handbook. Publisher: John Wiley & Sons, LTD, Editors (Sullivan, S., Cowan, C. A., Eggan, K.) Harvard University, Cambridge, MA, USA (2007); Human Stem Cell, a Laboratory Guide ($2^{nd}$ Edition) by Peterson, S., and Loring, J. F. (2012).

"Differentiating" and "differentiation": these terms, in the context of living cells, relate to progression of a cell further down the developmental pathway. A "differentiated cell" is a cell that has progressed further down the developmental pathway than the cell it is being compared with; differentiation is the process of progression. Human pluripotent stem cells can differentiate into lineage-restricted progenitor cells (cells that, like a stem cell, have a tendency to differentiate into a specific type of cell, but are already more differentiated than a stem cell and are pushed to eventually differentiate into its end-stage cell; e.g. endoderm, mesoderm and ectoderm), which in turn can differentiate into further restricted cells (e.g., cardiomyocyte progenitors, neuronal cell progenitors), which can differentiate into terminally differentiated cells (e.g., cardiomyocytes (e.g. atrial and ventricular cardiomyocytes) or neurons). Differentiation is controlled by the interaction of a cell's genes with the physical and chemical conditions outside the cell, usually through signaling pathways involving proteins embedded in the cell surface. In the present invention, "differentiation" is the biological process whereby an unspecialized human pluripotent stem cell (population) acquires the features of a specialized cell such as a cardiomyocytes, particularly cardiomyocytes having an atrial phenotype, under controlled conditions in in vitro culture. The human pluripotent stem cells may be exposed to the culture media compositions and methods of the invention so as to promote differentiation of the human pluripotent stem cells into cardiomyocytes, particularly cardiomyocytes having an atrial phenotype. Cardiac differentiation in general can be detected by the use of markers selected from, but not limited to, alpha actinin, NKX2-5, GATA4, myosin heavy chain, myosin light chain, troponin, and tropomyosin (Burridge et al (2012) Stem Cell Cell, Vol. 10(1):16-28, US2013/0029368). Within the context of the current invention, human pluripotent stem cell population are differentiated towards cardiomyocytes, preferably cardiomyocytes having or displaying an atrial phenotype, for example as witnessed by the presence of COUP-TFI and/or II in or on the cell or up-regulation of COUP-TFI and/or II levels in pluripotent stem cell-derived cardiomyocytes obtained by the methods of the present invention.

"Embryonic stem cells": abbreviated as 'ES cells' or ESC (or if of human origin 'hES cells' or 'hESCs') refers to stem cells that are derived from the inner cell mass of a blastocyst. The skilled person understands how to obtain such embryonic stem cells, for example as described by Chung (Chung et al (2008) Stem Cell Lines, Vol 2(2):113-117), which employs a technique that does not cause the destruction of the donor embryo(s). Various ESC lines are listed in the NIH Human Embryonic Stem Cell Registry. Pluripotent embryonic stem cells can be distinguished from other types of cells by the use of markers or lineage-specific markers including, but not limited to, Oct-4, Nanog, GCTM-2, SSEA3, and SSEA4.

"Exemplary": this terms means "serving as an example, instance, or illustration," and should not be construed as excluding other configurations disclosed herein.

"Induced pluripotent stem cell" or "iPSC": These terms refer to pluripotent stem cells that are derived from a cell that is not a pluripotent stem cell (i.e., from a cell this is differentiated relative to a pluripotent stem cell). Induced pluripotent stem cell can be derived from multiple different cell types, including terminally differentiated cells. Induced pluripotent stem cell generally have an hESC cell-like morphology, growing as flat colonies with large nucleocytoplasmic ratios, defined borders and prominent nuclei. In addition, induced pluripotent stem cell may express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing induced pluripotent stem cells may be found in, for example, U.S. Patent Publication Nos. US20090047263, US20090068742, US20090191159, US20090227032, US20090246875, and US20090304646. To generate induced pluripotent stem cells, somatic cells may be provided with reprogramming factors (e.g. Oct4, SOX2. KLF4, MYC, Nanog, Lin28, etc.) known in the art to reprogram the somatic cells to become pluripotent stem cells (see, for example, Takahashi et. al, Cell. 2007 Nov. 30; 131(5):861-72; Takahashi et. al, Nat Protoc. 2007; 2(12): 3081-9; Yu et. al, Science. 2007 Dec. 21:318(5858):1917-20. Epub 2007 Nov. 20).

"Markers" or "lineage-specific markers": these terms refer to a characteristic associated with the phenotype of cells of a lineage and can be used to assess the differentiation of cells. The terms may for example refer to nucleic acid or polypeptide molecules that are differentially expressed in a cell of interest. The detectable level of the marker is sufficiently higher or lower in the cells of interest compared to other cells, such that the cell of interest can be identified and distinguished from other cells using any of a variety of methods known in the art.

"Media": This term refers to an aqueous solution, including buffers, suitable for maintaining human or animal cells (e.g. pluripotent stem cells) for a sufficient period. For example, a media is suitable if it allows the treatment of cells (e.g. pluripotent stem cells) for a period required to obtain the effect intended by the treatment. The term "media" also, and preferably, includes growth media that are suitable for the in vitro cell culture and/or differentiation of human or animal cells. A "defined media" refers to a (growth) media suitable for the in vitro cell culture of human or animal cells and in which all of the chemical components are known. Such defined media does not or essentially not comprise any ill-defined source of nutrients and/or other ill-defined factors. Within the context of the current invention the defined media used may still contain defined amounts of products such as (purified) albumin, growth factors, and hormones, but is preferably essential free of serum (i.e. serum is less than 1% w/w, preferably less than 0.5% w/w. even more preferably less than 0.1% w/w, even more preferably less than 0.05% w/w of the media ready for use, most preferably the media is free of serum (i.e. 0% w/w serum; albeit it might contain defined amount of specified compounds like (recombinant) albumin. Although widely used, serum has many limitations. It contains high levels of numerous and unknown proteins and compounds which interfere dramatically with the small quantities of the desired proteins produced by the cells. The presence of serum may also affect in vitro testing results with the cells obtained since some compounds may bind up to 99% to serum proteins. Another limitation is the serum batch-to-batch inconsistencies, resulting in serious regulatory concern about various serum protein contaminations in the product.

"Pluripotency": This term is generally understood by the skilled person and refers to an attribute of a (stem) cell that has the potential to differentiate into all cells constituting one or more tissues or organs, for example, any of the three germ layers: endoderm (e.g. interior stomach lining, gastrointestinal tract, the lungs), mesoderm (e.g. heart, muscle, bone, blood, urogenital tract), or ectoderm (e.g. epidermal tissues and nervous system).

"Pluripotent stem cell" or "PSC": This is a stem cell capable of producing all cell types of the organism and can produce cells of the germ layers, e.g. endoderm, mesoderm, and ectoderm, of a mammal and encompasses at least pluripotent embryonic stem cells and induced pluripotent stem cells. Pluripotent stem cells can be obtained in different ways. Pluripotent embryonic stem cells may, for example, be obtained from the inner cell mass of an embryo. Induced pluripotent stem cells (iPSCs) may be derived from somatic cells. Pluripotent stem cells may also be in the form of an established cell line.

"Stem cells": Stem cells are a population of undifferentiated cells defined by their ability at the single cell level to both self-renew and differentiate to produce progeny cells, including self-renewing progenitors, non-renewing progenitors, and terminally differentiated cells (Morrison et al. (1997) Cell 88:287-298). Stem cells have the ability to divide for indefinite periods in culture. Stem cells are cells that may be stably multiplied and cultured in vitro and are totipotent, pluripotent, induced pluripotent, multipotent, oligopotent, or unipotent cells, preferably at least pluripotent. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts. Stem cells are categorized as somatic (adult) stem cells or embryonic stem cells. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

"Stem cell-derived cardiomyocytes" or "pluripotent stem cell-derived cardiomyocytes": These cells, or cardiomyocyte cell population, can be defined as spontaneously contractile cells derived by in vitro methods from a human pluripotent cell, although sometimes non-contractile cells can be obtained. Such cells still manifest other of the typical characteristics of cells that were in vitro differentiated into cardiomyocytes and are in the art also referred to as (in vitro obtained) stem-cell derived cardiomyocytes. Recent reviews defining and described stem-cell derived cardiomyocytes have covered methods to create (e.g. Vidarsson et al. Stem Cell Rev. 2010; 6(1):108-120, Boheler et al. Circ Res. 2002; 91(3):189-201. Mummery et al. Circ Res. 2012; 111(3):344-358, and Jiang et al. J Cell Mol Med. 2012; 16(8):1663-1668, David et al. Physiology (Bethesda) 2012; 27(3):119-129), and purify (Habib et al. J Mol Cell Cardiol. 2008; 45(4):462-474) such stem-cell derived cardiomyocytes, as well as their electrophysiology (Blazeski et al. Prog Biophys Mol Biol. 2012; 110(2):178-195), and these methods and media, for example based on APEL (StemCell Technologies) and StemPro34 (Invitrogen), used are well known to the skilled person. "Stem cell-derived cardiomyocytes" or "pluripotent stem cell-derived cardiomyocytes" may be, for instance, pluripotent stem cell-derived atrial cardiomyocytes as obtained by the methods of the invention, i.e. that display atrial markers such as COUP-TFI and/or II, preferably COUP-TF1/alpha actinin and/or COUP-TF1/alpha actinin.

"Somatic stem cell": an undifferentiated cell found in a differentiated tissue that can renew itself (clonal) and (with certain limitations) differentiate to yield all the specialized cell types of the tissue from which it originated.

"Undifferentiated": A stem cell that has not developed a characteristic of a more specialized cell is an undifferentiated cell. As will be recognized by one of skill in the art, the terms "undifferentiated" and "differentiated" are relative with respect to each other. A cells that is 'differentiated' has a characteristic of a more specialized cell. Differentiated and undifferentiated cells are distinguished from each other by several well-established criteria, including morphological characteristics such as relative size and shape, ratio of nuclear volume to cytoplasmic volume; and expression characteristics such as detectable presence of known (gene) markers of differentiation.

DETAILED DESCRIPTION OF THE INVENTION

In a first aspect, the present invention relates to an in vitro (e.g. in culture flasks) method for differentiating human pluripotent stem cells into atrial cardiomyocytes, the method comprising the steps of:
a) contacting the human pluripotent stem cells with (an effective amount of) a Wnt-signaling agonist and/or a BMP-signaling agonist in an aqueous media for a period of about 6-54 hours;
b) after step a), contacting the Wnt-signaling agonist and/or BMP-signaling agonist-contacted cells with (an effective amount) of a Wnt-signaling antagonist in an aqueous media for a period of about 6-54 hours; and
wherein the cells are contacted with (an effective amount of) a retinoic acid-signaling agonist in an aqueous media within the first 96 hours of steps a) and b), for a period of at least 6 hours.

Preferably the human pluripotent stem cells are in the form of a monolayer.

It will be understood by the skilled person that providing the retinoic acid-signaling agonist in an aqueous media within the first 96 hours of steps a) and b) may include adding the retinoic acid-signaling agonist only during step a), only during step b), or both during step a) and step b). For example, after contacting cells with the Wnt-signaling antagonist of step a) for 48 hours, aqueous media may be replaced by aqueous media devoid of Wnt-signaling agonist but comprising a Wnt-signaling antagonist and a retinoic acid-signaling agonist and initiate step b) by incubating the cells in said medium for, for example 48 hours. It may also include the possibility that, 24 hours after initiation of step b), more retinoic acid-signaling agonist is added to the media.

It is understood that an "effective amount" of a drug or compound such as a Wnt-signaling agonist and/or BMP-signaling agonist and Wnt-signaling antagonist and retinoic acid-signaling agonist, refers to an amount sufficient to significantly produce an effect, i.e. globally causing or allowing treated pluripotent stem cells to differentiate into atrial cardiomyocytes of the present invention compared to untreated pluripotent stem cells (i.e. untreated pluripotent stem cells will not differentiate into atrial cardiomyocytes). An "effective amount" of a Wnt-signaling agonist and/or BMP-signaling agonist and Wnt-signaling antagonist and retinoic acid-signaling agonist may also refer to an amount sufficient to significantly increase the yield, number or ratio of cardiomyocytes having an atrial phenotype within a population of pluripotent stem cell-derived cardiomyocytes generated by the methods as taught herein.

The effective dose will depend on the Wnt-signaling agonist, BMP-signaling agonist, Wnt-signalling antagonist and/or retinoic acid-signalling agonist employed in the methods of the present invention.

In an embodiment, depending on the type of Wnt-signaling agonist used, the effective amount or dose of the Wnt-signaling agonist may typically be at least about 0.1 microM. at least about 1 microM, at least about 2.5 microM, at least about 5 microM, and usually not more than about 500 microM, not more than about 250 microM, not more than about 100 microM, not more than about 50 microM. In some embodiments the effective amount is around about 3 to 7 microM, preferably about 5 microM.

In an embodiment, depending on the type of BMP-signaling agonist used, the effective amount or dose of the BMP-signaling agonist may typically be at least about 0.1 microM, at least about 1 microM, at least about 2.5 microM, at least about 5 microM, and usually not more than about 500 microM, not more than about 250 microM, not more than about 100 microM, not more than about 50 microM. In some embodiments the effective amount is around about 3 to 7 microM, preferably about 5 microM.

In an embodiment, depending on the type of Wnt-signaling antagonist used, the effective amount or dose of the Wnt-signaling antagonist may typically be about 0.02-10 microM, preferably about 0.05-9 microM, more preferably about 0.07-8 microM, more preferably about 0.1-7 microM, more preferably about 0.15-6 microM, and even more preferably about 0.2-5 microM.

In an embodiment, depending on the type of retinoic acid signaling agonist used, the effective amount or dose of the retinoic acid agonist may typically be an amount that produce or cause effects equivalent to those produced or caused by retinoic acid used at a concentration of about at least 2 microM, more preferably about 5-15 microM, most preferably about 10 microM. It was surprisingly found that a, in a preferred embodiment, a minimal concentration of at least 2 microM of retinoic acid-signaling agonist is used. It was found that such concentrations further promote the differentiation of human pluripotent stem cells into atrial cardiomyocytes. Concentrations of less than 2 microM of retinoic acid-signaling agonist (e.g. 1 microM of retinoic acid) may not, or to a lesser extent, promote efficient differentiation of human pluripotent stem cells into atrial cardiomyocytes, e.g. as assessed by the presence/absence of atrial cardiomyocyte markers such as COUP-TFI and COUP-TFII. In other words, it was surprisingly found that cardiomyocytes having a more developed homogenous atrial phenotype may be obtained when using concentrations of the retinoic acid signaling agonist equivalent to the concentration of retinoic acid as disclosed above and in combination with the other aspects of the method disclosed herein. This is surprising in view of the limited understanding of the pathways involved in differentiation into atrial cardiomyocytes, and more in particular when a particular pathway is active. Even more limited is the understanding on if and how different pathway interact in atrial differentiation, and in case there is a connection between pathways, at what moment during differentiation this interaction is relevant.

In particular, the combination of having a retinoic acid signaling agonist, preferably having a concentration of the retinoic acid signaling agonist equal to at least 2 microM retinoic acid, and the contacting of the cells therewith within the first 96 hours of steps a) and b), as disclosed and embodied herein, for a period of at least 6 hours is preferred. It is further understood that depending on the particular drug component used in the media as taught herein, i.e. Wnt-signaling agonist, BMP-signaling agonist, Wnt-signaling antagonist or retinoic acid-signaling agonist used, the effective amount or dose of each drug component may be separately optimized around the ranges as taught herein so as to observe or enhance the desired effect, i.e. causing or allowing treated pluripotent stem cells to differentiate into atrial cardiomyocytes of the present invention (i.e. cardiomyocytes having an atrial phenotype of the invention) compared to untreated pluripotent stem cells. For instance, different Wnt-signaling antagonists, such as XAV-939 and IWP-L6 may be present in the aqueous media as taught herein in a concentration of about 5 microM and 0.25 microM, respectively, in concordance with the ranges as taught herein. The skilled person knows how to find an optimal effective amount or dose for a particular drug component as taught, based on the ranges above, herein without undue burden.

In an embodiment, step a) is for a period of about 24-48 hours, i.e. the human pluripotent stem cells are contacted with a Wnt-signaling agonist and/or a BMP-signaling agonist in an aqueous media for a period of about 24-48 hours, more preferably 48 hours.

In an embodiment step b) is for a period of about 24-48 hours, i.e. the Wnt-signaling agonist and/or BMP-signaling agonist-contacted cells are contacted with a Wnt-signaling antagonist in an aqueous media for a period of about 24-48 hours, preferably 48 hours.

In a preferred embodiment, step a) is for a period of about 24-48 hours, i.e. the human pluripotent stem cells are contacted with a Wnt-signaling agonist and/or a BMP-signaling agonist in an aqueous media for a period of about 24-48 hours, more preferably 48 hours, and step b) is for a period of about 24-48 hours, i.e. the Wnt-signaling agonist and/or BMP-signaling agonist-contacted cells are contacted with a Wnt-signaling antagonist in an aqueous media for a period of about 24-48 hours, preferably 48 hours.

It was surprisingly found by the present inventor that, contacting the cells as taught herein, with an effective amount of a retinoic acid-signaling agonist, preferably retinoic acid (e.g. all-trans retinoic acid), in an aqueous media within the first 96 hours of steps a) and b), preferably 24-48 hours after initiating step a), for a period of at least 6 hours, preferably 24-48 hours, the pluripotent stem cells were induced to undergo atrial differentiation or were induced to take a developmental pathway leading to atrial differentiation eat an earlier stage of differentiation, i.e. within 4 days of initiating differentiation (e.g. 4 days after initiating step a) of the methods of the invention), compared to what is achievable by traditional methods where induction towards atrial differentiation could not be realized before 4 days after initiating differentiation in culture and where differentiation with a retinoic acid-signaling agonist could only be started after at least 4 days of cultivation or differentiation.

It is understood that contacting the cells as taught herein, with an effective amount of a retinoic acid-signaling agonist, preferably retinoic acid (e.g. all-trans retinoic acid), in an aqueous media within the first 96 hours of steps a) and b) means that the retinoic acid-signaling agonist (e.g. retinoic acid) is added or provided concomitantly while preforming step (a) and/or (b) and not after step (b). In other words, this means that, according to the method disclosed herein, the retinoic acid signaling agonist is contacted with the cells at least concomitantly/at the same time with the Wnt-signaling agonist and/or the BMP-signaling agonist or concomitantly/at the same time with the Wnt-signaling antagonist and/or both (i.e. in step a) and/or step b)).

Preferably the retinoic acid signaling agonist is used concomitantly/at the same time with the Wnt-signaling antagonist.

Preferably, the concomitant use (i.e. being present at the same time) as described above is for at least 2, 4, or 6 hours in step a) and/or at least 2, 4, or 6 hours in step b). Preferably, during the whole period that the cells are contacted with the retinoic acid signaling agonist, the Wnt-signaling agonist and/or the BMP-signaling agonist is also present (during step a)), and/or the Wnt-signaling antagonist is also present (during step b)). Although not preferred, it is not excluded that part of the contacting of the cells with the retinoic acid signaling agonist is performed after step b).

In other words, it was found that contacting the pluripotent stem cells with a retinoic acid-signaling agonist (e.g. retinoid acid) within the first 96 hours (or 4 days) of initiating step a), which corresponds to initiating differentiation, for a period of at least 6 hours, caused or induced the pluripotent stem cells (e.g. hiPSC) to undergo atrial differentiation at an earlier stage of development (i.e. earlier after differentiation was initiated), than with traditional methods. The pluripotent stem cell-derived cardiomyocytes obtained by the methods of the invention (i.e. induced to undergo atrial differentiation at an early stage, e.g. within 4 days of initiating step a)) typically manifest an atrial phenotype (e.g. as exemplified by, for example, the expression of atrial markers like COUP-TFI and/or COUP-TFII, preferably COUP-TF1/alpha actinin and/or COUP-TF1/alpha actinin) after steps a) and b) of the method of the invention, i.e. about 7, 8, 9, 10, 11, 12, 13, more preferably 14 days or later after initiating step a).

With the method of the invention, a cell culture enriched in atrial cardiomyocytes, displaying a more mature phenotype (i.e. a more atrial like phenotype) may be obtained. The percentage of cells displaying an atrial phenotype is increased relative to a treatment as described herein but wherein no retinoic acid signaling agonist is used.

In a preferred embodiment, the step of contacting the human pluripotent stem cells with a retinoic acid-signaling agonist (e.g. retinoic acid) is performed within the first 96 hours of steps a) and b), preferably within the first 90, 84, 78, 72, 66, 60, 54, 48 hours of steps a) and b). Depending on the length of step a), the step of contacting the human pluripotent stem cells with the retinoic acid-signaling agonist may thus be at step a) and/or step b).

In the step of contacting the cells with a retinoic acid-signaling agonist, the period of exposure to the retinoic acid-signaling agonist is at least 6 hours, preferably 12, 18, 24, 30, 36, 42, 48 hours, for example between 6-54 hours or 12-48 hours. /pct It was also found that the method as taught herein, as a whole, allowed for the production of higher yields of pluripotent stem cell-derived atrial cardiomyocytes (i.e. having an atrial phenotype compared to traditional methods. The term "higher or increased yield" as used herein refers to a significantly increased yield or level or amount. Generally, the yield or level associated with a test sample (i.e. pluripotent stem cells contacted with a Wnt-signaling agonist, BMP-signaling agonist, Wnt-signaling antagonist and retinoic acid-signaling agonist according to the method of the invention) is increased when it is at least 1%, 2%, 3%, 4%, 5%, such as 10%, 15%, 20%, 25%, 30%, 35%, 40%, 45%, 50% higher or more than the corresponding yield or level in a control sample or reference sample (i.e. pluripotent stem cells not contacted with a Wnt-signaling agonist, BMP-signaling agonist, Wnt-signaling antagonist and retinoic acid-signaling agonist according to the method of the invention or treated the same way, but without the addition of the retinoic acid signaling agonist). In other words, with the methods of the invention, it is possible to obtain more (greater amount, quantity) human pluripotent stem cell-derived atrial cardiomyocytes of the invention, e.g. express or display atrial markers such as COUP-TFI and/or II, preferably COUP-TF1/alpha actinin and/or COUP-TF1/alpha actinin) compared to what is achieved with traditional methods.

It was also found that the method as taught herein, as a whole, allowed for the production of pluripotent stem cell-derived atrial cardiomyocytes, i.e. having a more developed or mature atrial phenotype compared to traditional methods, as determined for example by detecting the presence or expression of atrial markers such as KCNA5, COUP-TFI and/or II, preferably COUP-TF1/alpha actinin and/or COUP-TF1/alpha actinin.

In a preferred embodiment, the step of contacting the cells with a retinoic acid-signaling agonist in an aqueous media is performed for a period of about 24-48 hours, at any point during the first 96 hours of initiating step a). For instance, the cells as taught herein may be contacted with the retinoic acid-signaling agonist for a period of about 24-48 hours (e.g. for a period of 25, 30, 35, 40, 45 hours), within 48 hours of initiating step a) (e.g. within 1, 5, 10, 15, 20, 25, 30, 35, 40, 45 hours after initiating step a)) or upon initiating step b).

In a preferred embodiment, the cells as taught herein may be contacted with the retinoic acid-signaling agonist for about 24-48 hours (e.g. for a period of 25, 30, 35, 40, 45 hours), about 48 hours after initiating step a) or upon initiating step b), most preferably after step a), e.g. when step a) was for a period of about 48 hours.

In an embodiment, it may be advantageous (e.g. for obtaining a higher yield of atrial cardiomyocytes) to contact the cells as taught herein with the retinoic acid-signaling agonist for a period of about 24-48 hours (e.g. for a period of 25, 30, 35, 40, 45 hours), about 48 hours after initiating step a) and upon initiating step b), i.e. after step a), e.g. when step a) was for a period of about 48 hours. Thus, it may be advantageous to contact the cells as taught herein with both the Wnt-signaling antagonist and the retinoic acid-signaling agonist for a period of about 24-48 hours (e.g. for a period of 25, 30, 35, 40, 45 hours), about 48 hours after initiating step a) and upon initiating step b), e.g. when step a) was for a period of about 48 hours.

In other words, and in general, it was found that better results are obtained (e.g. a higher yield of atrial cardiomyocytes may be generated) when the human pluripotent stem cells are contacted with both the Wnt-signaling antagonist and the retinoic acid-signaling agonist, preferably for a period of about 24-48 hours, about 48 hours of initiating step a) and upon initiating step b), i.e. after step a) when step a) was for about 48 hours. Simply put, in a preferred embodiment the cells are treated with the Wnt-signaling agonist and/or BMP agonist in step a) for a period of about 24-48 hours. After this period, the cells are treated with the Wnt-signaling antagonist and with the retinoic acid-signaling agonist, preferably for a period of about 24-48 hours.

In an embodiment, it may be advantageous contact the cells with an aqueous media not comprising a BMP-signaling agonist in step a). Specifically, it may be advantageous to contact the cells with an aqueous media only comprising a Wnt-signaling agonist in step a). In other words, it may be advantageous to perform the method as taught herein as follows:
a) contacting the human pluripotent stem cells with a Wnt-signaling agonist in an aqueous media for a period of about 6-54 hours;
b) after step a), contacting the Wnt-signaling agonist-contacted cells with of a Wnt-signaling antagonist in an aqueous media for a period of about 6-54 hours; and wherein the cells are contacted with a retinoic acid-signaling agonist in an aqueous media within the first 96 hours of steps a) and b), for a period of at least 6 hours.

In an embodiment, the cells may be contacted with an aqueous media not comprising a Wnt-signaling antagonist after step b). For instance, the treatment with the Wnt-signaling antagonist may be terminated at the term of step b) by refreshing the media as taught herein by a media devoid of Wnt-signaling antagonist (and, for that matter, also devoid of Wnt-signaling agonist or BMP-signaling agonist). Such aqueous growth media after step b) may or may not comprise (effective amounts of) retinoic acid-signaling agonists as taught herein.

In an embodiment, the retinoic acid-signaling agonist is provided to the cells within about 24-72 hours (for instance within 30, 35, 40, 45, 50, 55, 60, 65, preferably 72 hours) after the Wnt-signaling agonist and/or BMP-signaling agonist is provided to the cells in step a) (which may include, preferably, adding the retinoic acid-signaling agonist during step b)).

In an embodiment, the retinoic acid-signaling agonist of is provided to the cells within about 24-48 hours (for instance within 30, 35, 40, preferably 48 hours) after the Wnt-signaling agonist and/or BMP-signaling agonist is provided to the cells in step a.

In a preferred embodiment, the retinoic acid-signaling agonist is provided to the cells 24-48 hours (for instance within 30, 35, 40, preferably 48 hours) after the Wnt-signaling agonist and/or BMP-signaling agonist is provided to the cells in step a).

In a further preferred embodiment, the retinoic acid-signaling agonist is provided together with the Wnt-signaling antagonist to the cells about 24-48 hours after the Wnt-signaling agonist and/or BMP-signaling agonist is provided to the cells in step a), e.g. when step a) was for a period of about 24-48 hours (for instance with 30, 35, 40, preferably 48 hours). The skilled person understands that in step b) the aqueous growth media does not comprise the Wnt-signaling agonist and the BMP-signaling agonist of step a).

In an embodiment, the retinoic acid-signaling agonist in an aqueous media may be provided to the cells at more than one time point during the first 96 hours of steps a) and b). For instance, the retinoic acid signaling agonist in an aqueous media may be provided twice to the cells, the first time after about 24 hours of initiating step a) and the second time after about 48 hours of initiating step a) or of initiating step b). In a preferred embodiment, the retinoic acid signaling agonist in an aqueous media may be provided twice to the cells, the first time about 48 hours of initiating step a) and the second time about 72 hours of initiating step a). For example, in case step b) starts 48 hours after initiation of step a), the retinoic acid-signaling agonist may be provided together with the Wnt-signaling antagonist at the initiation of step b), 24 hours later followed by adding additional retinoic acid-signaling agonist (i.e. 72 hours after initiation of step a)).

In an embodiment, any suitable Wnt-signaling agonist and/or BMP-signaling agonist, Wnt-signaling antagonist and retinoic acid-signaling agonist may be used in the methods as taught herein.

The skilled person is well-aware of the terms "Wnt-signaling agonist", "BMP-signaling agonist", "Wnt-signaling antagonist" and "retinoic acid-signaling agonist". As such, a "Wnt-signaling agonist" increases output from the β-Catenin dependent Wnt signaling pathway while a "Wnt-signaling antagonist" decreases output from the β-Catenin dependent Wnt signaling pathway. A BMP-signaling agonist increases the output of BMP signaling.

A retinoic acid-signaling agonist is an agent that stimulates retinoic acid signaling pathway in a cell, e.g. a pluripotent stem cell as taught herein. The term "retinoic acid signaling" refers to the actions or effects (direct and indirect) of retinoid acid on a cell. Retinoic acid, for example, acts by binding to the retinoic acid receptor (RAR), which is bound to DNA as a heterodimer with the retinoid X receptor (RXR) in regions called retinoic acid response elements (RAREs). Binding of the retinoic acid ligand to RAR alters the conformation of the RAR, which affects the binding of other proteins that either induce or repress transcription of a nearby gene (including Hox genes and several other target genes). Retinoic acid receptors mediate transcription of different sets of genes controlling differentiation of a variety of cell types, thus the target genes regulated depend upon the target cells. In some cells, one of the target genes is the gene for the retinoic acid receptor itself (RAR-beta in mammals), which amplifies the response. In the present invention, the term "retinoid acid-signaling agonist" includes RAR agonists (e.g. isotretinoin, AC261066, AC55649, adapalene, AM580, AM80, BMS753, BMS961, CD1530, CD2314, CD437, Ch55, tazarotene, TTNPB, TTNB, LG100268 and LGD1069), RXR agonists (e.g. bexarotene, CD3254, docosahexaenoic acid (DHA), fluorobexrotene, SR11237), synthetic retinoids (e.g. EC23, fenretinide) as well as stable analogues or chemical equivalents thereof.

During early development, the retinoic acid signaling pathway is critical in the patterning and development of the heart and promotes cardiogenesis. The retinoic acid signaling pathway in the stem cells can be stimulated by any suitable treatment or agent (e.g. retinoic acid-signaling agonist as taught herein). In one example, the retinoic acid-signaling pathway in the pluripotent stem cells is stimulated by contacting the stem cells with a retinoic acid-signaling agonist such as retinoic acid or vitamin A or all-trans retinoic acid. In another example, the retinoic acid-signaling pathway in the pluripotent stem cell is stimulated by contacting the pluripotent stem cells with a retinoic acid-signaling agonist such as a retinoic acid receptor agonist, such as CH55, TTNB, LG100268 and LGD1069.

In an embodiment, the Wnt-signaling agonist may be an inhibitor of GSK-3β, BIO, CHIR 98014, BIO-acetoxime, BIO, LiCl, SB 216763, SB 415286, AR A014418, 1-Azakenpaullone, Bis-7-indolylmaleimide or CHIR-99021 or a combination thereof.

In a more preferred embodiment, the Wnt-signaling agonist may be CHIR-99021.

In an embodiment, the BMP-signaling agonist may be selected from the group of BMP2, BMP4 and activin, or a combination thereof.

In a preferred embodiment, the BMP-signaling agonist may be BMP4.

In an embodiment, the Wnt-signaling antagonist may be selected from the group of C59, IWR-1, IWP-2, IWP-4, XAV-939, IWP-L6 and DKK-1, or a combination thereof.

In a preferred embodiment, the Wnt-signaling antagonist may be IWP-L6 in combination with XAV-939. It was surprisingly found that when this combination of Wnt-signaling antagonists was used in the methods as taught herein, the efficiency of differentiation and/or yield of human pluripotent stem cell-derived atrial cardiomyocytes (as determined for example by detecting the presence of expression of atrial markers such as COUP-TFI and/or II, preferably COUP-TF1/alpha actinin and/or COUP-TF1/alpha actinin) was increased.

In an embodiment, the retinoic acid-signaling agonist may be selected from the group of vitamin A, retinoic acid, all-trans retinoic acid, a retinoic acid receptor agonist, and CH55, TTNB, LG100268, LG1069, or a combination thereof.

It is understood that depending on the type of retinoic acid signaling agonist used, the effective amount or dose of the retinoic acid agonist may typically be an amount that produce or cause effects equivalent to those produced or caused by retinoic acid (e.g. all-trans retinoic acid) used at a concentration of about at least 2 microM, more preferably about 5-15 microM, most preferably about 10 microM.

It was surprisingly found that by using a retinoic acid-signaling agonist, preferably all-trans retinoic acid, at a concentration of at least 2 microM, more preferably 5-15 microM, most preferably 10 microM, a significant increase in the efficiency of differentiation of human pluripotent stem cell-derived into atrial cardiomyocytes of the invention and/or increase in yield (amount, quantity) of these cells, was observed. Particularly good results were obtained when the retinoic acid-signaling agonist used in the methods as taught herein was all trans retinoic acid used at a concentration of 10 microM. It was further observed that when the retinoic acid-signaling agonist, (e.g. all trans retinoic acid), was used in the methods as taught herein at a concentration below 2 microM, no significant effect on the efficiency of differentiation and/or yield of atrial cardiomyocytes was observed.

In an embodiment, the human pluripotent stem cells for use in the methods of the invention may be selected from the group of embryonic stem cells, fetal stem cells, somatic stem cells, or induced pluripotent stem cells (e.g. human induced pluripotent stem cells). In the present invention, the human pluripotent stem cells were obtained using a technique that does not cause the destruction of the donor embryo(s), for example as described in Chung et al (2008) Stem Cell Lines, Vol. 2(2), pages 113-117.

In a preferred embodiment, the human pluripotent stem cells are human induced pluripotent stem cells. In an embodiment, the induced pluripotent stem cells are prepared from a non-pluripotent cell, typically an adult somatic cell, or terminally differentiated cell, such as fibroblast, a hematopoietic cell, a myocyte, a neuron, an epidermal cell, or the like, by introducing or contacting reprogramming factors (Yamanaka Cell 2009 and Yamanaka Nat Rev Mol Cell 2012). The examples refer to several means and methods for producing induced pluripotent stem cells, however, various other methods are known to the person skilled in the art.

In a most preferred embodiment, the method as taught herein is carried out without the presence of a BMP-signaling agonist but only in the presence of a Wnt-signaling agonist, and may be further characterized in that:
the Wnt-signaling agonist in step a) may be CHIR-99021, preferably in a concentration of 3-7 microM in the aqueous medium;
the Wnt-signaling antagonist in step b) may be a combination of XAV-939, preferably in a concentration of 0.1-10 microM in the aqueous media and IWP-L6, preferably in a concentration of 0.02-2.5 microM in the aqueous media; and
the retinoic acid agonist may be retinoic acid, preferably all-trans retinoic acid, preferably in a concentration of at least 2 microM, more preferably 5-15 microM, most preferably 10 microM.

In further most preferred embodiment, the method as taught herein is characterized in that:
the Wnt-signaling agonist and/or BMP-signaling agonist of step a) may be provided to the human pluripotent stem cells at t=0 hours;
the Wnt-signaling antagonist of step b) may be provided a t=24-72 hours, preferably at 24-48 hours; and
and the retinoic acid-signaling agonist may be provided at t=24-72 hours, preferably at 24-48 hours.

It is understood that the expression "t=0 hours" corresponds to the initiation of step a) or in other words, it corresponds to the initiation of differentiation of human pluripotent stem cells into atrial cardiomyocytes (e.g. as determined by the expression or presence of atrial markers such as COUP-TF-I and/or II once the cells start beating around day 10, preferably co-expression or co-presence of COUP-TFI and/or COUP-TFII with another cardiomyocyte markers, such as those taught herein, e.g. COUP-TFI and/or COUP-TFII with alpha actinin). Thus the expression "t=24-72 hours" means that the Wnt-signaling antagonist and/or retinoic acid-signaling agonist may be provided to the cells 24-72 hours after initiating step a) (i.e. which begins at t=0). In an embodiment, the media of step a) is preferably devoid of BMP-signaling for the same advantageous reasons as mentioned above.

In a further aspect, the present invention relates to an in vitro (culture) method for inducing COUPTFII and/or COUPTFI expression in human cardiomyocytes, the method comprising performing the steps of the method as taught herein. It is understood that human pluripotent stem cell-derived cardiomyocytes expressing COUPTFII and/or COUPTFI are cardiomyocytes having an atrial phenotype, i.e. atrial cardiomyocytes within the context of the current invention.

In a further aspect, the present invention relates to an in vitro (culture) method for differentiating a human pluripotent stem cell into a atrial cardiomyocytes, the method comprising the step of:
a) stimulating Wnt-signaling and/or BMP-signaling in the human pluripotent stem cell for a period of about 6-54 hours;
b) after step a), inhibiting Wnt-signaling and/or BMP-signaling for a period of about 6-54 hours; and wherein retinoic acid signaling is stimulated in the cells within the first 96 hours of steps a) and b), for a period of at least 6 hours.

In a preferred embodiment, the present invention relates to an in vitro (culture) method for differentiating a human pluripotent stem cell into an atrial cardiomyocyte, the method comprising the steps of
a) stimulating Wnt-signaling and/or BMP-signaling in the human pluripotent stem cell for a period of about 6-54 hours; and subsequently
b) inhibiting Wnt-signaling and stimulating retinoic acid signaling in the Wnt-signaling stimulated cells of step a) for a period of about 6-54 hours.

In the methods above, stimulating the Wnt-signaling and/or BMP-signaling in the human pluripotent stem cell can be performed as taught above, i.e. by contacting the cells with (an effective amount of) a Wnt-signaling agonist (e.g. CHIR98014) and/or BMP-signaling agonist (e.g. activin).

Inhibiting the Wnt-signaling in the Wnt-signaling and/or BMP-signaling stimulated cells can be performed as taught above, i.e. by contacting the cells with (an effective amount of) a Wnt-signaling antagonist (e.g. IWP-L6 in combination with XAV-939).

Stimulating the retinoic acid signaling in the cells as taught above can be performed as taught herein, i.e. by contacting the cells with (an effective amount of) a retinoic acid-signaling agonist (e.g. all trans retinoic acid).

Preferences and preferred embodiments for this method are as set-out above.

In an embodiment, the step a) is performed for 24-48 hours, preferably 48 hours.

In an embodiment, step b) is performed within 24-72 hours after the start of step a), preferably 48 hours.

In an embodiment, step b)) is performed for 24-48 hours, preferably 48 hours.

In the present invention, the aqueous media of step a) comprising a Wnt-signaling agonist and/or a BMP-signaling agonist can be refreshed one or more times, i.e. replaced by a different media, for instance an aqueous media comprising a Wnt-signaling antagonist with or without a retinoic-signaling agonist or may be replaced by the same media (i.e. aqueous media comprising the Wnt-signaling agonist and/or BMP-signaling agonist). Similarly, the aqueous media of step b) comprising Wnt-signaling antagonist with or without a retinoic-signaling agonist may be refreshed one or more times, i.e. replaced by a different media, for instance an aqueous media devoid of Wnt-signaling antagonist and with or without retinoic acid-signaling agonist or may be replaced by the same media (i.e. aqueous media comprising a Wnt-signaling antagonist with or without a retinoic-signaling agonist). The skilled person can determine, based on the present disclosure, when and how many times the media of step a) and/or b) should be refreshed within the context of the method steps of the present invention The skilled person understands that any type of media suitable for maintaining and/or cultivating the human pluripotent stem cells can be used in the methods as taught herein. In an embodiment, the aqueous media is preferably a serum-free media.

The term "aqueous media" as used herein refers to a composition that is water-based or to a composition in which the solvent is water. For instance, an aqueous media can be obtained from dissolving (any) water-soluble substance(s) into water. Preferably the media is comprised with compounds and nutrients that support growth of the human pluripotent stem cells, particularly differentiation of human pluripotent stem cells into atrial cardiomyocytes, as determined for instance by the presence of expression of atrial markers such as COUP-TFI and/or II (including transcripts thereof), preferably COUP-TF1/alpha actinin and/or COUP-TF1/alpha actinin).

In the methods as taught above, after step b), the method may further comprise the step of cultivating the pluripotent stem cell-derived atrial cardiomyocytes as obtained as a result of the steps a) and b) of the method, in an aqueous growth media devoid of Wnt-signaling agonist, BMP-signaling agonist, Wnt-signaling antagonist and retinoic acid-signaling agonist for a period of at least 5 days, for example 5, 6, 7, 8, 9, 10, 11, 12, 13, 14, 15, 16, 17, preferably 18 days or more. Any growth media suitable for cultivating cardiomyocytes, e.g. atrial cardiomyocytes of the invention may be used for this purpose. For instance, when step b) ends at 4 days after initiating step a), the atrial cardiomyocytes may be further cultured until 5, 6, 7, 8, 9, 10, 11, 12, 13, 14, 15, 16, 17, preferably 18 days after initiating step a).

In an embodiment, the methods as taught herein may further comprise the step of verifying the presence of cardiomyocytes having differentiated into atrial cardiomyocytes (i.e. having acquired an atrial phenotype) at about 7, 8, 9, 10, 11, 12, 13, more preferably 14 days or later after initiating step a. Such verifying may involve, for example determining a cardiomyocyte electrophysiological profile; determining responsiveness to known cardioactive drugs (e.g. AF drugs having specificity for atrial ion channels); or analyzing the cell population for the presence or absence of specific atrial cardiomyocyte marker proteins or genes such as, but not limited to, COUP-TFI and/or II, preferably COUP-TF1/alpha actinin and/or COUP-TF1/alpha actinin as taught above.

Alternatively or simultaneously, verifying the presence of cardiomyocytes having differentiated into or acquired an atrial phenotype can be determined by methods known to the skilled person, for examples methods that look at phenotype, morphology, gene expression, metabolic markers, cell surface markers, electrophysiological characteristics and/or cellular functional assay of the cell.

Atrial Cardiomyocytes

In a further aspect, the present invention relates to atrial cardiomyocytes or human pluripotent stem cell-derived cardiomyocytes having an atrial phenotype obtainable by or obtained with any of the methods as taught herein.

In the present invention, the human pluripotent stem cell-derived atrial cardiomyocytes i.e. having an atrial phenotype, as obtained by any of the methods described above, will typically display or express atrial markers, for instance, but not limited to, COUP-TFI and/or II, after examining the cells at about 7, 8, 9, 10, 11, 12, 13, more preferably 14 days or later after initiating step a. In a preferred embodiment, the atrial phenotype is confirmed by detecting the co-expression or co-presence of COUP-TFI and/or COUP-TFII with another cardiomyocyte markers, such as those taught herein, e.g. COUP-TFI and/or COUP-TFII with alpha actinin, in the pluripotent stem cell-derived cardiomyocytes obtained by the methods of the invention, at about 7, 8, 9, 10, 11, 12, 13, more preferably 14 days or later after initiating step a).

Compositions

In a further aspect, the present method relates to a composition or a pharmaceutical composition comprising the atrial cardiomyocytes, i.e. which are obtainable by any of the methods as taught herein.

In an embodiment, the composition as taught herein may comprise an effective amount of the atrial cardiomyocytes produced by the above methods, and optionally a pharmaceutically acceptable carrier or excipient and/or preservation agents or other molecules suitable for preserving the cardiomyocytes alive and/or functional. The skilled person knows how to select a carrier, excipient, preservation agent and the like suitable for the compositions of the invention.

In another embodiment, the composition may comprise at least about 50%, preferably, at least about 60%, 70%, 80%, 90%, 95%, 99%, or 100% atrial cardiomyocytes.

In an embodiment, the compositions as taught comprise other cell types such as endothelial cells, smooth muscle cells and/or fibroblast cells, and the like.

In an embodiment, the compositions as taught herein may be comprised in a kit, for instance a kit for assays for drug screening, drug testing, etc.

Uses

In a further aspect, the present invention relates to the use of the atrial cardiomyocytes as taught herein, i.e. obtainable by any of the methods as taught herein, for any suitable purposes, e.g. suitable uses in the field of cardiology or cardiac diseases, cardiac research and/or cardiac tissue engineering or tissue repair, and the like.

In an embodiment, the atrial cardiomyocytes as taught herein may be used for drug screening or drug discovery. For instance, the atrial cardiomyocytes as taught herein may be used to identify a modulator of cardiomyocytes (e.g. modulator of an atrial cardiomyocytes) by contacting an atrial cardiomyocyte produced by the above methods with a test substance and measuring the effect of the test substance on a property of the atrial cardiomyocytes (e.g. electrophysiological properties, action potential (AP), calcium metabolism or signaling, gene expression pattern or signature, morphology, contractibility, frequency of beatings, survival, and combination thereof, etc) and compare the results with those obtained from measuring the property of the atrial cardiomyocyte not contacted with the test substance. Thus, if the results show that the property(ies) of the atrial cardiomyocyte contacted with the test substance is/are different from that of the atrial cardiomyocyte not contacted with the test substance, then the results identify the test substance as a modulator, e.g., a stimulator or inhibitor, of the property of the atrial cardiomyocytes.

In one example, an increase of the property of the atrial cardiomyocyte contacted with the test substance relative to that of the atrial cardiomyocyte not contacted with the test substance identifies the test substance as a stimulator of the property of the atrial cardiomyocyte. In another example, a decrease of the property of the atrial cardiomyocyte contacted with the test substance relative to that of the atrial cardiomyocyte not contacted with the test substance identifies the test substance as an inhibitor of the property of the atrial cardiomyocyte.

By comparing the results obtained with the atrial cardiomyocytes obtained with the method of the invention with results obtained with ventricular cardiomyocytes, selectivity of a modulator for atrial versus and/or ventricular cardiomyocytes may be determined.

In a preferred embodiment, the atrial cardiomyocytes or human pluripotent stem cell-derived atrial cardiomyocytes as taught herein may be used for drug screening or drug discovery of atrial fibrillation (AF) drugs for the treatment of AF in subjects. The term "atrial fibrillation" (AF) as used herein refers to a condition or disease characterized by an abnormal heart rhythm presenting as rapid rhythm with irregular heart beating. AF is the most common abnormal heart rhythm in Europe and North America, affecting about 2% to 3% of the population, particularly aging population. AF may be accompanied by heart palpitations, fainting, shortness of breath, and/or chest pain. AF increases the risk of heart failure, dementia, and stroke. Hypertension and valvular heart disease are the most common risk factors for AF but other heart-related risk factors include heart failure, coronary artery disease, cardiomyopathy, and congenital heart disease. Other factors include obesity, sleep apnea excess alcohol intake, diabetes mellitus, and thyrotoxicosis. AF is often treated with medications that slow the heart rate to a near normal range or that convert the heart rhythm to normal sinus rhythm. However, existing drugs, such as antiarrhythmic agents, often lack atrial selectivity and pose the risk of inducing undesirable cardiac events, such as ventricular proarrhythmia. Therefore, there is a clear need for new, effective AF drugs devoid of these limitations. There is also a need for new disease models for AF, particularly AF model for AF drug screening and/or AF drug discovery.

The discovery or identification of new, more effective AF drugs (e.g. more sensitive, less side effects) is problematic because AF drugs in general are known to modulate cardiac properties present in the atria and ventricles, which cause them to have a narrow therapeutic index and in some cases are associated with life threatening safety issues. Ideally, AF drugs should selectively modulate targets such as ion channels present only in the atria and not the ventricle. Another limitation is the lack of effective and sensitive cell model for screening of AF drugs.

Therefore, it may be advantageous to use the atrial cardiomyocytes as taught herein in AF drug screening or discovery process or assay to preclude the need for atrial tissue (biopsy) from a donor, which may be difficult to obtain and/or cause discomfort to the donor, to increase throughput capacity (e.g. allow testing of a large library of test compounds in a short time period), efficiency, and/or sensitivity of the assay, and/or decrease labor and/or costs, and others. It may also be advantageous to use the atrial cardiomyocytes as taught herein to generate new AF disease model for drug screening and/or AF drug discovery. Recent genome-wide association studies have identified genetic variants in a number of chromosomal regions that are associated with AF) (e.g. PITX2, CAV1, MYOZ1, C9orf3 and FANCC, and others). Pluripotent stem cells (e.g. iPSC) derived from AF patients carrying one or genetic variants may be used as a source to generate cardiomyocytes with an atrial phenotype for research purposes and/or drug screening, and others.

Alternatively, it may be advantageous to use atrial cardiomyocytes as obtained from the methods of the invention and ventricular cardiomyocytes, for comparison purposes, for assessing the atrial or ventricular specificity and/or sensitivity of a given a test compound, i.e. in other words for assessing whether the test compound specifically or selectively modulates ion channel or other targets present only in the atria and not the ventricle, or the other way around. For instance, test compounds that only elicit a response or change in property(ies) (e.g. electrophysiological properties, AP, gene expression, ion channel signaling, etc) in atrial cardiomyocytes and not in ventricular cardiomyocytes will be identified as a selective modulator of atrial cardiomyocytes, for example atrial ion channels, and thus may I be identified as a good candidate for a AF drug. Methods or procedures for assessing atrial specificity of test compound is provided for example in Milnes et al (2012) Drug Discovery Today. Vol. 17, Numbers 13/14.

Having now generally described the invention, the same will be more readily understood through reference to the following examples which is provided by way of illustration and is not intended to be limiting of the present invention.

EXAMPLES

Example 1: Method of Culturing the Cells

The purpose of this step was to proliferate the human induced Pluripotent stem cells (hiPSC) so as to obtain a sufficient number of hiPSC for use in the differentiation method of example 2 below.

Procedure: hiPSC were cultured on feeders (mouse embryonic fibroblasts) with DMEM/F-12, GlutaMAX medium supplemented with 20% Knockout™ Serum Replacement, 1% NEAA, 10 ng/ml b-FGF, and 0.1 mM β-mercaptoethanol or under feeder-free conditions using Essential 8™ Medium (Life Technologies) on vitronectin (VTN-N) coated plates according to the manufacturer's instructions, or using L7 culture system (Lonza) according to manufacturer's instructions. Cells were routinely passaged using Accutase (Sigma-Aldrich) in case of feeder cultures or using 0.5 mM EDTA for E8 cultures or using L7 passaging solution in case of the L7 culture system. The cell cultures were maintained in a humidified incubator at 37° C. with 5% $CO_2$. See, for example, http://hpscreg.eu/cell-line/CRMi003-A for NCRM-1 cells.

Example 2: Method for Differentiation of hiPSC into Atrial Cardiomyocytes

The purpose of this experiment was to determine the influence of retinoic acid (RA) (i.e. all-trans retinoic acid was used in the experiments below) on differentiation of hiPSC into atrial cardiomyocytes. Specifically, the influence of all-trans retinoic acid concentration (1 microM vs 10 microM) as well as the effect of timing/duration of retinoic acid application (i.e. d2-4 vs d3-d4 vs d2-18) were tested according to the following experimental scheme:

TABLE 1

Treatment groups and experimental conditions.

| Treatment groups | Experimental conditions |
|---|---|
| 1 | 10 microM RA/d 2-4 |
| 2 | 10 microM RA/d 3-4 |
| 3 | 1 microM RA/d 3-4 |
| 4 | 1 microM RA/d 2-18 |

Abbreviation:
d: day;
RA: all-trans retinoic acid

Aqueous Media

The aqueous media consisted of the following composition: 46.5% IMDM (Gibco 21056), 0.25% Bovostar BSA, 46.5% Ham's F12 with Glutamax, 2 mM Glutamax, 450 nM alphaMTG, 0.05 mg/ml ascorbic acid, 0.5% 5000 U/ml Pen/Strep (Gibco 12070), 0.01% 1000*Trace elements mix B (Cellgro 99-176-CL), 0.1% 1000*Trace elements mix C (Cellgro 99-176-CL). The aqueous media was used in all four treatment groups, except that RA was added at different concentrations depending on the given treatment group, i.e. 10 microM for treatment group 1 and 2 and 1 microM for treatment groups 3 and 4.

Wnt-Signaling Agonist

For all treatment groups, CHIR-99021 was used at a concentration of 5 microM.

Wnt-Signaling Antagonists

For all experimental groups, a combination of 5 microM of XAV-939 and 0.25 microM of IWP-L6 was used.

Plating of hiPSC hiPSC were seeded in 12-well plates at density of 60.000 cells per well or a split ratio that was empirically determined to give 30-80% confluence after 4 days. Culture media was replaced after 4 days, in each treatment group, with a differentiation media as described in Table 1.

Method of Differentiation for Treatment Group 1:

Step a): The hiPSC were contacted with 5 microM of CHIR-99021 for a period of 48 hours. At the term of step a), the media was refreshed, i.e. replaced by a media devoid of CHIR-99021 and comprising 5 microM of XAV-939 and 0.25 microM of IWP-L6.

Step b): Immediately after having refreshed the medium of step a), i.e. immediately after the 48 hours of step a) (which correspond to 2 days after having initiated step a), the cells were contacted with 5 microM of XAV-939 and 0.25 microM of IWP-L6 as well as with 10 microM of all trans retinoic acid. The cells were cultured in this media for 48 hours. At the term of step b), the media was refreshed with a media but devoid of CHIR-99021, XAV-939, and IWP-L6. The hiPSC-derived cardiomyocytes were further cultured until 14 days after initiating step a), after which they were harvested and submitted to immunohistochemical procedure for assessment of atrial phenotype (see example 3 below).

Method of Differentiation for Treatment Group 2:

Step a): The hiPSC were contacted with 5 microM of CHIR-99021 for a period of 48 hours. At the term of step a), the media was refreshed, i.e. replaced by a media devoid of CHIR-99021 and comprising 5 microM of XAV-939 and 0.25 microM of IWP-L6.

Step b): Immediately after having refreshed the medium of step a), i.e. immediately after the 48 hours of step a), the cells were contacted with 5 microM of XAV-939 and 0.25 microM of IWP-L6. At 24 hours after initiating step b) (which corresponds to 3 days after having initiated step a), 10 microM of retinoic acid was added to the media of step b). The cells were cultured in this media for 24 hours. At the term of step b), the media was refreshed with a media but devoid of CHIR-99021, XAV-939, and IWP-L6. The hiPSC-derived cardiomyocytes were further cultured until 14 days after initiating step a), after which they were harvested and submitted to immunohistochemical procedure for assessment of atrial phenotype (see example 3 below).

Method of Differentiation for Treatment Group 3:

Step a): The hiPSC were contacted with 5 microM of CHIR-99021 for a period of 48 hours. At the term of step a), the media was refreshed, i.e. replaced by a media devoid of CHIR-99021 and comprising 5 microM of XAV-939 and 0.25 microM of IWP-L6.

Step b): Immediately after having refreshed the medium of step a), i.e. immediately after the 48 hours of step a), the cells were contacted with 5 microM of XAV-939 and 0.25 microM of IWP-L6. At 24 hours after initiating step b) (which corresponds to 3 days after having initiated step a), 1 microM of retinoic acid was added to the media of step b). The cells were cultured in this media for 24 hours. At the term of step b), the media was refreshed with a media but devoid of CHIR-99021, XAV-939, and IWP-L6. The hiPSC-derived cardiomyocytes were further cultured until 14 days after initiating step a), after which they were harvested and submitted to immunohistochemical procedure for assessment of atrial phenotype (see example 3 below).

Method of Differentiation for Treatment Group 4:

Step a): The hiPSC were contacted with 5 microM of CHIR-99021 for a period of 48 hours. At the term of step a), the media was refreshed, i.e. replaced by a media devoid of CHIR-99021 and comprising 5 microM of XAV-939 and 0.25 microM of IWP-L6.

Step b): Immediately after having refreshed the medium of step a), i.e. immediately after the 48 hours of step a) (which correspond to 2 days after having initiated step a), the cells were contacted with a media comprising 5 microM of XAV-939 and 0.25 microM of IWP-L6 as well as with 1 microM of retinoic acid. The cells were cultured in this media for 48 hours. At the term of the 48 hours, the media was refreshed with a media devoid of CHIR-99021, XAV-939, and IWP-L6 and comprising 1 microM of retinoic acid (in other words, the retinoic acid treatment was continued without CHIR-99021, XAV-939, and IWP-L6). The hiPSC-derived cardiomyocytes were further cultured in this media until 18 days after initiating step a). At day 18, the cells were harvested and submitted to immunohistochemical procedure for assessment of atrial phenotype (see example 3 below).

Example 3: Verifying the Phenotype

The atrial markers COUP-TFI and COUP-TFII were used indicator of atrial phenotype as taught herein. The cardiomyocyte marker alpha actinin was used to confirm that cells displaying or expressing COUP-TFI and COUP-TFII were hiPSC-derived cardiomyocytes.

The hiPSC-derived cardiomyocytes obtained from each of the experimental group above were submitted to an immunohistochemical procedure to detect the co-presence or co-expression of COUP-TFI and COUP-TFII in combination with alpha actinin (i.e. co-staining with COUP-TFI and alpha actinin as well as co-staining with COUP-TFII and alpha actinin), using antibodies against COUP-TFI, COUP-TFII and alpha actinin.

Briefly the hiPSC-derived cells were fixed in 4% paraformaldehyde (PFA) and transferred to coverslips within a new 24-well plate. The cells were then processed for immunohistochemistry using a mouse COUP-TFII primary antibody (R&D Systems, cat. No. PP-H&147-00) at a concentration of 1:100, a rabbit COUP-TFI [EPR10841] primary antibody (Abcam, cat. no. ab181137) at a concentration of 1:100 and a rabbit alpha actinin antibody (Abcam, cat. No. ab68167) at a concentration of 1:500. Secondary antibodies used were Donkey anti-rabbit igG (H+L) antibody Alexa Flour 488 (Life Technologies, cat. No. A21206) at a concentration of 1:500 and goat anti-mouse IgG, Cy3-Affinipure (Sanbio, cat. No. 115-165-146) at a concentration of 1:250.

At the term of the immunohistochemistry procedure, the immunostained hiPSC-derived cells from each experimental group were photographed for (qualitative) analysis of the immunoreactivity signal for COUP-TFI and COUP-TFII (see example 4 below).

Example 4: Qualitative Assessment of the Intensity of the Immunoreactivity Signal for COUP-TFI and COUP-TFII in hiPSC-Derived Cardiomyocytes The intensity of the immunoreactivity signal (i.e. fluorescence staining) for COUP-TFI and COUP-TFII in the hiPSC-derived cardiomyocytes obtained from each experimental group was (qualitatively) visually assessed from images. The qualitative assessment of the intensity of the immunoreactivity signal for COUP-TFI and COUP-TFII was carried out in hiPSC-derived cells costained with COUP-TFI/alpha actinin and COUP-TFII/alpha actinin. Costaining for COUP-TFI and alpha actinin was used as a confirmation that the hiPSC-derived cells taken into the analysis were cardiomyocytes (i.e. as determined by the presence of alpha actinin) having acquired an atrial phenotype (i.e. as determined by the presence of COUP-TFI and/or COUP-TFII).

The intensity of the immunoreactivity signal for COUP-TFI and COUP-TFII (i.e. fluorescence staining) was compared between immunostained hiPSC-derived cardiomyocytes obtained from each experimental group. The results of the qualitative analysis are reported as follows:

TABLE 2

| Qualitative assessment | |
|---|---|
| Symbols | Meaning |
| +++ | Strongest immunoreactivity signal (i.e. fluorescence staining) |
| ++ | Moderate immunoreactivity signal (i.e. fluorescence staining) |
| + | Lowest immunoreactivity signal (i.e. fluorescence staining) |
| +/− | Marginal immunoreactivity signal (i.e. fluorescence staining) (i.e. very low signal, not consistently observed in all cells). |
| − | No immunoreactivity signal (i.e. fluorescence staining) |

Results

The results of the phenotype analysis are presented in Table 3 below. Specifically, the results show that retinoic acid significantly influenced the differentiation of hiPSC into cardiomyocytes having an atrial phenotype, however under certain conditions.

The results show that the differentiation of hiPSC into cardiomyocytes having an atrial phenotype is best (i.e. is robust, i.e. strongest immunoreactive signal for COUP-TF1 and/or COUP-TF1) when retinoic acid is added at more than 1 microM, in particular as can be seen at a concentration of 10 microM, at a timing corresponding to 2 days after initiating differentiation (or in other words, 48 hours after initiating step a of the method, and for a duration of 48 hours (see experimental group I above and Table 3 below).

The results also show that good results, although not as robust as observed above for group 1 (i.e. moderate immunoreactive signal for COUP-TF1 and/or COUP-TF1), can be obtained when retinoic acid is added at a concentration of 10 microM, at a timing corresponding to 3 days after initiating differentiation (or in other words, 72 hours after initiating step a of the method, and for a duration of 24 hours (see experimental group 2 above and Table 3 below).

The results further show that when retinoic acid is added at a concentration of 1 microM, at a timing corresponding to 2 days after initiating differentiation (or in other words, 48 hours after initiating step a of the method, and for a duration of 12 days (see experimental group 4 above and Table 3 below), a limited effect of retinoic acid on differentiation of hiPSC into atrial cardiomyocytes is observed (i.e. low immunoreactive signal for COUP-TF1 and/or COUP-TF1).

No effect of (all-trans) retinoic acid on differentiation of hiPSC into atrial cardiomyocytes was observed (i.e. marginal or no immunoreactive signal for COUP-TF1 and/or COUP-TF1) when retinoic acid was added at a concentration of 1 microM, at a timing corresponding to 3 days after initiating differentiation (or in other words, 72 hours after initiating step a of the method, and for a duration of 24 hours (see experimental group 3 above and Table 3 below).

TABLE 3

Qualitative assessment of the intensity of the immunoreactivity signal for COUP-TFI and COUP-TFII in hiPSC derived-cardiomyocytes in response to retinoic acid treatment (i.e. all-trans retinoic acid), where retinoic acid concentration, timing and duration of retinoic acid exposure were varied.

| Treatment groups | Experimental conditions | COUP-TFI | COUP-TFII |
|---|---|---|---|
| 1 | 10 microM RA/d 2-4 | ++ | +++ |
| 2 | 10 microM RA/d 3-4 | + | ++ |
| 3 | 1 microM RA/d 3-4 | − | − |
| 4 | 1 microM RA/d 2-14 + 4 | +/− | + |

The invention claimed is:

1. An in vitro method of differentiating human pluripotent stem cells into mature atrial cardiomyocytes expressing COUPTFII and COUPTFI, the method comprising the steps of:
   a) culturing the human pluripotent stem cells in an aqueous media containing 1-7 µM of a Wnt-signaling agonist and/or a BMP-signaling agonist for a period of about 24-54 hours;
   b) culturing the Wnt-signaling agonist and/or BMP-signaling agonist-treated cells obtained from step (a) in an aqueous media containing 0.1-10 µM of a Wnt-signaling antagonist for a period of about 24-54 hours, wherein during step b) the Wnt-signaling agonist and/or BMP-signaling agonist-treated cells are provided with 2-10 µM of retinoic acid or all-trans retinoic acid within the first 72 hours of step a) and b) and wherein the cells are treated with retinoic acid or all-trans retinoic acid for a period of at least 24 hours; and
   c) replacing the aqueous medium of the cells obtained after step (b) with an aqueous medium devoid of the Wnt-signaling agonist and/or BMP-signaling agonist and devoid of the Wnt-signaling antagonist such that mature atrial cardiomyocytes expressing COUPTFII and COUPTFI are obtained.

2. The method according to claim 1, wherein in step a) the culturing the human pluripotent stem cells in the aqueous medium containing the Wnt-signaling agonist and/or a BMP-signaling agonist is for a period of about 24-48 hours and/or wherein in step b) culturing the Wnt-signaling agonist and/or BMP-signaling agonist treated cells in the aqueous media containing the Wnt-signaling antagonist is for a period of about 24-48 hours.

3. The method according to claim 1, wherein the Wnt-signaling agonist and/or BMP-signaling agonist treated cells are provided with the retinoic acid or all-trans retinoic acid in an aqueous media is for a period of about 24-48 hours.

4. The method of claim 1, wherein in step a) the cells are cultured in the aqueous media not comprising a BMP-signaling agonist.

5. The method of claim 1, wherein the Wnt-signaling agonist is an inhibitor of GSK-3β, BIO, CHIR 98014, BIO-acetoxime, BIO, LiCl, SB 216763, SB 415286, AR A014418, 1-Azakenpaullone, Bis-7-indolylmaleimide, CHIR-99021, or a combination thereof.

6. The method of claim 1, wherein the BMP-signaling agonist is BMP2, BMP4, activin, or a combination thereof.

7. The method of claim 1, wherein the Wnt-signaling antagonist is C59, IWR-1, IWP-2, IWP-4, XAV-939, IWP-L6, DKK-1, or a combination thereof.

8. The method of claim 1, wherein the human pluripotent stem cells are embryonic stem cells or induced pluripotent stem cells.

9. The method of claim 1, wherein no BMP-signaling agonist is used, and wherein:
   the Wnt-signaling agonist in step a) is CHIR-99021 in a concentration of 3-7 µM in the aqueous medium;
   the Wnt-signaling antagonist in step b) is a combination of XAV-939 in a concentration of 0.1-10 µM in the aqueous media and IWP-L6 in a concentration of 0.02-2.5 µM in the aqueous media; and
   retinoic acid or all-trans retinoic acid is in a concentration of between 2 µM-10 µM.

10. The method according to claim 1, wherein in step (c) the aqueous medium devoid of the Wnt-signaling agonist and/or BMP-signaling agonist and devoid of the Wnt-signaling antagonist comprises 2-10 µM of retinoic acid or all-trans retinoic acid.

11. The method according to claim 1, wherein the cells are treated with retinoic acid or all-trans retinoic acid for a period of at least 48 hours.

12. The method according to claim 1, wherein 5-10 µM retinoic acid or all-trans retinoic acid is provided.

13. The method according to claim 1, wherein 10 µM retinoic acid or all-trans retinoic acid is provided.

* * * * *

UNITED STATES PATENT AND TRADEMARK OFFICE
CERTIFICATE OF CORRECTION

| | |
|---|---|
| PATENT NO. | : 11,773,375 B2 |
| APPLICATION NO. | : 16/088227 |
| DATED | : October 3, 2023 |
| INVENTOR(S) | : Stefan Robbert Braam, Ana Catarina Martins Grandela and Karin Langenberg |

It is certified that error appears in the above-identified patent and that said Letters Patent is hereby corrected as shown below:

On the Title Page

Page 2, item (57) reads:
"The present invention is in the field of pluripotent stem cells, more particularly cardiomyocytes derived from pluripotent stem cells. The present invention provides a novel method for differentiating human pluripotent stem cells into a population of cardiomyocytes having an atrial phenotype, and use of said atrial cardiomyocytes for screening of drugs, AF disease model, and others. The method of the invention is particularly useful to generate cardiomyocytes having a more developed or mature atrialphenotype and/or to generate higher yield of cardiomyocytes having an atrialphenotype."
Whereas it should read:
"The present invention is in the field of pluripotent stem cells, more particularly cardiomyocytes derived from pluripotent stem cells. The present invention provides a novel method for differentiating human pluripotent stem cells into a population of cardiomyocytes having an atrial phenotype, and use of said atrial cardiomyocytes for screening of drugs, AF disease model, and others. The method of the invention is particularly useful to generate cardiomyocytes having a more developed or mature atrial phenotype and/or to generate higher yield of cardiomyocytes having an atrial phenotype."

In the Claims

Claim 5, Column 26, Line 13 reads:
"BIO-acetoxime, BIO, LiCl, SB 216763, SB 415286, AR"
Whereas it should read:
"BIO-acetoxime, LiCl, SB 216763, SB 415286, AR"

Signed and Sealed this
Twenty-sixth Day of March, 2024

Katherine Kelly Vidal
*Director of the United States Patent and Trademark Office*

Page 1 of 1